United States Patent
Pang et al.

(10) Patent No.: US 9,999,399 B2
(45) Date of Patent: Jun. 19, 2018

(54) METHOD AND SYSTEM FOR PIGTAIL CATHETER MOTION PREDICTION

(75) Inventors: Yu Pang, Philadelphia, PA (US);
Yefeng Zheng, Dayton, NJ (US);
Matthias John, Nürnberg (DE); Jan Boese, Eckental (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 278 days.

(21) Appl. No.: 13/297,373

(22) Filed: Nov. 16, 2011

(65) Prior Publication Data
US 2012/0123250 A1 May 17, 2012

Related U.S. Application Data (60) Provisional application No. 61/414,038, filed on Nov. 16, 2010.

(51) Int. Cl.
*A61B 6/00* (2006.01)
*A61B 6/12* (2006.01)
*G06T 7/246* (2017.01)
*G06T 7/277* (2017.01)

(52) U.S. Cl.
CPC ............ *A61B 6/487* (2013.01); *A61B 6/12* (2013.01); *A61B 6/5264* (2013.01); *G06T 7/246* (2017.01); *G06T 7/277* (2017.01); *G06T 2207/10121* (2013.01); *G06T 2207/30021* (2013.01)

(58) Field of Classification Search
CPC ......... G06T 7/2073; G06T 2207/10121; G06T 2207/30021; G06T 7/2033; G06T 7/246; G06T 7/277; A61B 34/20; A61B 6/032; A61B 6/12; A61B 6/4014; A61B 6/466; A61B 6/487; A61B 6/504; A61B 6/5264
USPC .................... 128/704; 382/130; 600/425
See application file for complete search history.

(56) References Cited

U.S. PATENT DOCUMENTS

| | | | |
|---|---|---|---|
| 5,265,617 A * | 11/1993 | Verrier et al. | 600/517 |
| 6,961,608 B2 | 11/2005 | Hoshino et al. | |
| 7,920,911 B2 | 5/2011 | Hoshino et al. | |
| 7,940,971 B2 * | 5/2011 | Zhang et al. | 382/128 |

(Continued)

OTHER PUBLICATIONS

A. Brost et al. Respiratory motion compensation by model-based catheter tracking during EP procedures. Special Issue on the 12th International Conference on Medical Image Computing and Computer-Assisted Intervention (MICCAI) 2009.*

(Continued)

*Primary Examiner* — Michael Kahelin
*Assistant Examiner* — Helene Bor (57) ABSTRACT

A method and system for autoregressive model based pigtail catheter motion prediction in a fluoroscopic image sequence is disclosed. Parameters of an autoregressive model are estimated based on observed pigtail catheter tip positions in a plurality of previous frames of a fluoroscopic image sequence. A pigtail catheter tip position in a current frame of the fluoroscopic image sequence is predicted using the fitted autoregressive model. The predicted pigtail catheter tip position can be used to constrain pigtail catheter tip detection in the current frame. The predicted pigtail catheter tip position may also be used to predict abnormal motion in the fluoroscopic image sequence.

26 Claims, 8 Drawing Sheets

(56) References Cited

U.S. PATENT DOCUMENTS

| | | | |
|---|---|---|---|
| 2007/0217514 A1* | 9/2007 | Kumar | G06T 7/2073 375/240.16 |
| 2009/0062641 A1* | 3/2009 | Barbu et al. | 600/424 |
| 2009/0297005 A1* | 12/2009 | Heigl | 382/130 |
| 2010/0034446 A1* | 2/2010 | Zhu et al. | 382/130 |
| 2010/0157041 A1* | 6/2010 | Klaiman | G06T 7/0022 348/77 |
| 2010/0239148 A1 | 9/2010 | Zheng et al. | |
| 2010/0249579 A1 | 9/2010 | Starks | |
| 2011/0164035 A1 | 7/2011 | Liao et al. | |

OTHER PUBLICATIONS

Ren et al. "Adaptive prediction of respiratory motion for motion compensation radiotherapy" Phys. Med. Biol. 52 (2007) 6651-6661.*

* cited by examiner

METHOD AND SYSTEM FOR PIGTAIL CATHETER MOTION PREDICTION

This application claims the benefit of U.S. Provisional Application No. 61/414,038, filed Nov. 16, 2010, the disclosure of which is herein incorporated by reference.

BACKGROUND OF THE INVENTION

The present invention relates to medical imaging, and more particularly, to automatic prediction of pigtail catheter motion in a fluoroscopic image sequence.

Aortic valve disease affects a large number of people globally and is the most common type of valvular disease in developed countries. Implantation of a prosthetic aortic valve is often necessary to replace a severely damaged native valve. Although open-chest valve surgery is a well established procedure, minimally invasive transcatheter aortic valve implantation (TAVI) is an emerging technique, especially for high-risk patients, to minimize the surgical trauma. Interventional surgeries, such as TAVI, are typically performed under the guidance of real time fluoroscopic (x-ray) images. As the minimally invasive TAVI technique is emerging, physicians increasingly focus on minimizing the risks and making the surgery less invasive in order to minimize the trauma, especially for high-risk patients. For example, it is desirable to reduce the times of exposure to and the amount of the potentially toxic contrast agent that is injected into a patient's blood. Most of such contrast injections are used to highlight the aorta and coronaries in fluoroscopic images in order to visually guide physicians as to where the vessels are. Accordingly, it is desirable to provide an aortic mask overlay throughout the image sequences in order to perform the same function as the contrast agent to reduce contrast injection times.

BRIEF SUMMARY OF THE INVENTION

The present invention provides a method and system for automatically predicting motion of a pigtail catheter in a sequence of fluoroscopic images. Embodiments of the present invention utilize an autoregressive model based pigtail catheter motion prediction method. Since the pigtail catheter has the same motion as the aorta, it is possible to track the aorta by tracking the pigtail catheter instead.

In one embodiment of the present invention, parameters of an autoregressive model are estimated based on observed pigtail catheter tip positions in a plurality of previous frames of a fluoroscopic image sequence. A pigtail catheter tip position in a current frame of the fluoroscopic image sequence is predicted using the fitted autoregressive model. The pigtail catheter tip position can then be detected in the current frame based on the predicted pigtail catheter tip position. The predicted pigtail catheter tip position may also be used to predict abnormal motion in the current frame of the fluoroscopic image sequence.

These and other advantages of the invention will be apparent to those of ordinary skill in the art by reference to the following detailed description and the accompanying drawings.

DETAILED DESCRIPTION

The present invention is directed to a method and system for automatically predicting motion of a pigtail catheter in a fluoroscopic image sequence. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
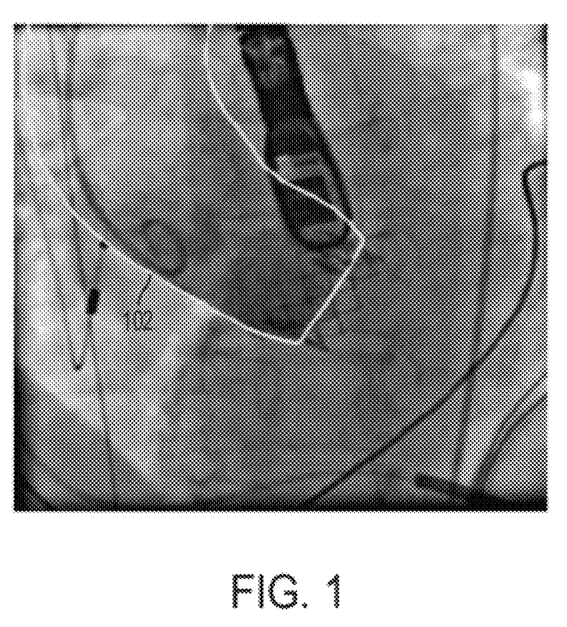
FIG. 1 illustrates an exemplary silhouette based overlay of an extracted aorta model on a 2D fluoroscopic image.

In order to reduce the amount of contrast injected into a patient, it is desirable to provide an aortic mask throughout the image sequences in order to perform the same function as the contrast. More specifically, a 3D mesh of the aorta can first be extracted from C-arm CT data and then overlaid onto a 2D fluoroscopic image. To finely overlay the mask, a projection matrix is applied first. Then by using the connectivity of 3D mesh points, an efficient silhouette extraction algorithm is performed to acquire the final aortic mask as described in U.S. patent application Ser. No. 13/35,802, filed on Sep. 19, 2011, and entitled "Method and System for Efficient Extraction of a Silhouette of a 3D Mesh", which is incorporated herein by reference. FIG. 1 illustrates an exemplary silhouette based overlay 102 of an extracted aorta model on a 2D fluoroscopic image. In clinical practice, physicians often prefer such mask can be seen throughout the sequence to guide an interventional procedure. However, due to the cardiac and respiratory motion, a static aorta mask throughout a fluoroscopic image sequence is not accurate.

In aortic valve implantation surgery, a pigtail catheter is inserted inside the aorta to inject contrast agent. When the contrast agent is injected through the catheter, the aorta and the valve are visible for a short period of time. Since the catheter is always inside the aorta and often inserted deep into the aortic valve leaflet pocket, the pigtail catheter tip has the same motion as the aortic valve. In this scenario, the pigtail catheter tip provides an important clue to track aortic valve motion. In embodiments of the present invention, the pigtail catheter tip is tracked to give the guidance of the aortic valve during the surgery. However, in this scenario, the aorta and pigtail catheter are highly influenced by the cardiac motion and respiratory motion, but conventional tracking methods only consider a simple motion model (e.g., static object or constant velocity). Such tracking methods are inadequate and embodiments of the present invention provide a motion model that is desirable for tracking a pigtail catheter in a fluoroscopic image sequence.

Embodiments of the present invention provide an autoregressive model based pigtail catheter motion prediction method to help in tracking the pigtail catheter in a fluoroscopic image sequence. Embodiments of the present invention utilize residual error criterion to determine the model order of the autoregressive model. The motion prediction method uses previous observation and predicted data to fit the model for predicting next time interval recursively. Such autoregressive model can be used in many applications in transcatheter aortic valve implantation (TAVI). For example, under many tracking-by-detection frameworks, detected results may drift away or be picked up wrongly. Autoregressive model prediction can be used as a search range constraint or a spatial penalty function to score the multiple candidates and help to select the correct candidate. Also, since the autoregressive model assumes that the target's motion is following a certain pattern, it can be used in abnormal movement detection. If the observation is far from the predicted position, it is possible to claim that anomalous motion is detected. This model will work for 2D/3D registration as well, and the results may be used in a temporal manner as the initial position estimation for the registration. The present invention is not limited to applications in TAVI, and may also be applicable to other interventional surgeries, such as left atrium fibrillation ablation, as well.

Autoregressive models are models dealing with time series data that aim to reveal the dynamic nature of the data, understand the data, and predict future values from the data. Embodiments of the present invention utilize the Autoregressive Moving Average (ARMA) model for predicting motion of an object, such as a pigtail catheter, in a sequence of medical images. The ARMA model consists of two parts: an autoregression part and a moving average part. The autoregression part uses previous observations in the sequence to predict the next observation. In particular, the autoregression part uses a linear combination of pigtail catheter locations in a number of previous frames of a fluoroscopic image sequence to predict the position in the next frame. The autoregression part is defined as:

$$X_t = c + \sum_{i=1}^{p} \alpha_i X_{t-i} + \varepsilon_t, \quad (1)$$

where $X_i$ denotes the object position in frame i, c is a constant, $\varepsilon_t$ is considered as Gaussian white noise $N(0,\sigma^2)$, $\alpha_i$ is the weighting coefficient for the observation of each previous frame and p is (abbreviated to AR(p)) is the order which indicates how many previous observations are used in the autoregressive part of the ARMA model.

The moving average part of the ARMA model is based on the error in previous observations and is expressed as:

$$X_t = \mu + \varepsilon_t + \sum_{i=1}^{q} \beta_i \varepsilon_{t-i}, \quad (2)$$

where $\mu$ is the expectation of $X_t$, $\varepsilon_t$ is the Gaussian white noise described above, $\varepsilon_{t-i}$ is the actual error for the previous frame t–i, and $\beta_i$ is the weighting coefficient for the error of each previous frame, and q (abbreviated to MA(q)) is the order which indicates how many previous observations are used in the moving average part of the ARMA model.

Combining the two parts together results the ARMA model with orders p and q as ARMA(p,q), which is expressed as:

$$X_t = c + \varepsilon_t + \sum_{i=1}^{p} \alpha_i X_{t-i} + \sum_{i=1}^{q} \beta_i \varepsilon_{t-i}, \quad (3)$$

By using the ARMA model, it is assumed that the time series is stationary and all white noises are independent identically distributed (i.i.d) random variables.

In order to apply the ARMA model for predicting pigtail catheter motion, the orders (p,q) can be selected based on a set of annotated training data so that the model will serve as a good representation. There are several possible ways to determine the orders. For example, an autocorrelation function (ac.f.) may be analyzed to identify if there is any certain pattern that can be used to select the order. Alternatively, the well-known F-test may be performed to determine if a chosen pair of p and q can represent the data well enough. Other possible criteria include the Akaike Information Criterion (AIC):

$$AIC = \log V + \frac{2d}{N}, \quad (4)$$

and Akaike Final Prediction Error (FPE):

$$FPE = V\left(\frac{1+d/N}{1-d/N}\right). \quad (5)$$

Both methods are based on cross validation testing, where V is a defined loss function, d is the number of estimated parameters, and N is the length of the dataset. When d<<N, the FPE will become:

$$FPE = V\left(1 + \frac{2d}{N}\right), \quad (6)$$

while AIC will become its logarithm form:

$$AIC = \log V. \quad (7)$$

Figure 2A:
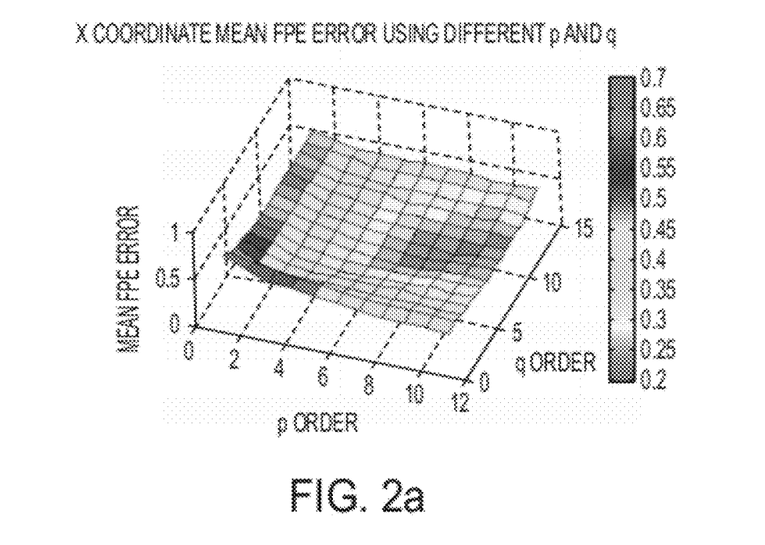
FIG. 2 illustrates exemplary order selection results.
Figure 2B:
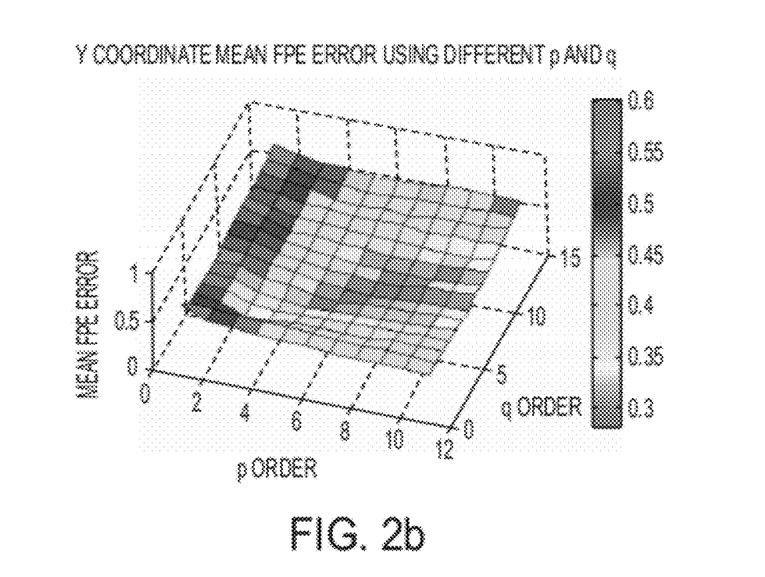

According to an advantageous implementation, for pigtail catheter tip motion prediction, FPE can be used as the main criterion for automatic selection of the order (p,q) based on the training data. Two separate models are built for X coordinate and Y coordinate assuming that there are no correlations between the two. Accordingly, two separate ARMA models can be used to predict the x coordinate and the y coordinate for the pigtail catheter tip. However, it is also possible to use a vector ARMA model, using both the x and y coordinates of the previous observation together to predict the motion of the pigtail catheter tip. FIG. 2 illustrates exemplary order selection results. As shown in FIG. 2, approximately 200 sequences were used to test all possible combinations of (p,q) for pigtail catheter tip motion prediction. The results show that FPE will reach a finite minimum point as the p and q orders increase. Image (a) of FIG. 2 shows exemplary results for the X coordinate and image (b) shows exemplary results for the Y coordinate. In this example, for the X coordinate, FPE will reach its minima at (9, 8), while for the Y coordinate, FPE will reach its minima at (6, 5).

Figure 3:
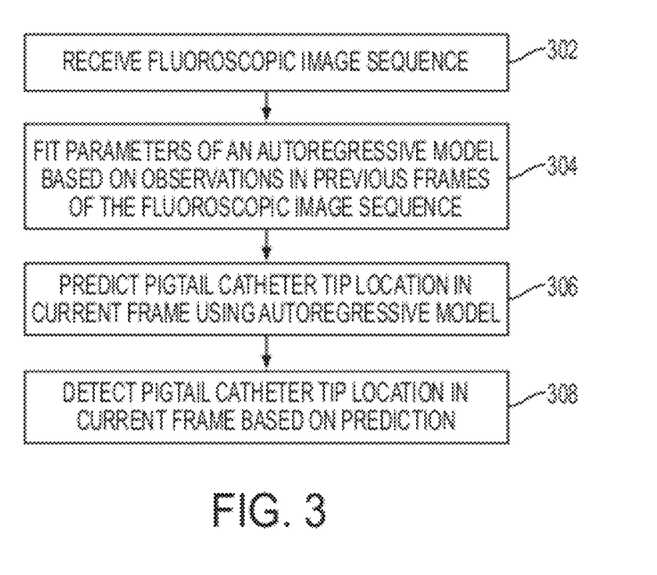
FIG. 3 illustrates a method for predicting motion of a pigtail catheter tip in a fluoroscopic image sequence according to an embodiment of the present invention.

FIG. 3 illustrates a method for predicting motion of a pigtail catheter tip in a fluoroscopic image sequence according to an embodiment of the present invention. As illustrated in FIG. 3, at step 302 a fluoroscopic image sequence is received. For example, the fluoroscopic image sequence can be received from an x-ray imaging device as the fluoroscopic image sequence is captured by the x-ray imaging device. It is also possible that the fluoroscopic image sequence is received by loading previously generated fluoroscopic images from a computer readable medium, or memory or storage of a computer system. The fluoroscopic image sequence is a temporal series of frames, in which each frame is a 2D fluoroscopic image. According to an advantageous embodiment, the fluoroscopic image sequence can be received by receiving fluoroscopic images from an x-ray imaging device in real time during an interventional procedure, such as a TAVI procedure. The x-ray imaging device may be a C-arm scanning device, but the present invention is not limited thereto.

At step 304, parameters of the autoregressive model are fit based on observations in previous frames of the fluoroscopic image sequence. In particular, the parameters of c, $\alpha_i$, and $\beta_i$ of the ARMA model of equation (3) are estimated using observations from previous frames of the fluoroscopic image sequence. Given the previous observations $\{X_t\}$, least squares regression can be applied to find the parameters that will minimize:

$$S = \sum_{t=1}^{N} (X_t - \hat{X}_t)^2 \quad (8)$$

where $\{X_t\}$ is the true values for the location of the pigtail catheter tip in the previous frames, and $\{\hat{X}_t\}$ is prediction values for the location of the pigtail catheter tip in the previous frames using the ARMA model of equation (3). S is the total error in the previous frames, and the goal is to find the parameters of the ARMA model that minimize S.

However, due to the MA part of the model with the pure random process, $\varepsilon_t$, the least squares solution cannot be explicitly found. One possible alternative solution is to set a starting guess for each parameter and assume that $\varepsilon_0=0$. Then, each $\varepsilon_t$ is calculated according to equation (3), the estimated residual sum of squares $\Sigma_{i=1}^{t} \varepsilon_i^2$ is calculated. Repeating this procedure by searching the neighboring values of the parameters results in a series of the sum of squares. Choosing parameters that minimize the value, will result in an approximation of the least square solution. This method of estimation requires an efficient searching strategy, such as hill-climbing, maximum likelihood estimation, etc.

The observations in the previous frame may be manually observed, for example by a physician performing the TAVI procedure, or may be automatically detected. In order to automatically detect the pigtail catheter tip in the frames, a learning-based pigtail catheter detector may be trained based on annotated training data and used to detect the location of the pigtail catheter tip in the previous frames. The learning-based pigtail catheter detector may be trained based on features extracted from the annotated training data using one or more probabilistic boosting trees (PBT). It is to be understood that an initial set of frames of the fluoroscopic image sequence may be used to generate observations without prediction, and these observations are then used to fit the parameters of an initial model and begin prediction (step 306). As more observations become available, the method can periodically return to step 304 to fit new parameters to the model based on all of the previous observations. For example, step 304 can be repeated prior to pigtail catheter tip location (step 306) and detection (step 308) in every frame so as to refit the model as soon as a new observation is available, or step 304 can be repeated to refit the model at a certain interval of frames to avoid intensive computation. Also, observations in the first few frames may not be sufficient to fit for high orders of p and q. In this case, lower orders of p and q are initially selected, and the orders of p and q are gradually increased to reach the orders determined based on the training data as more observations become available.

At step 306, the pigtail catheter tip location in current frame is predicted using the autoregressive model. In particular, once the parameters of the ARMA model are estimated, the location of the pigtail catheter is predicted in the current frame using the ARMA model of equation (3). In calculating the predicted location using equation (3), $\varepsilon_{t-1}$ are residual errors between previous observations $\{X_t\}$ and corresponding predicted results $\{\hat{X}_t\}$, while $\varepsilon_t$ is assumed to be 0, since a pure white noise at 0 has the highest probability.

At step 308, the pigtail catheter tip is detected in the current frame based on the predicted pigtail catheter tip location determined using the ARMA model. In particular, the prediction of the pigtail catheter tip location is used to constrain the search in the pigtail catheter tip tracking. In order to use the pigtail catheter motion prediction in a tracking scenario, the detection of pigtail catheter tip candidates in a frame can be constrained in multiple possible ways to help to select the correct candidate. Using a tracking-by-detection framework, a trained pigtail catheter tip detector is typically used to detect a number of pigtail catheter tip candidates in a frame and estimate the pigtail catheter tip location either by the ranking or aggregating the pigtail catheter tip candidates. However, both ranking and aggregation of candidates may be unreliable and could be ruined by false alarms. In order to improve the detection results, the motion prediction result can be integrated into the pigtail catheter tip detection to constrain the detection. In one embodiment, the search range for the trained pigtail catheter detector can be restricted to within a relaxed area generated with respect to the predicted position of the pigtail catheter tip. In another embodiment, a penalty function, such as a 2D Gaussian distribution centered at the predicted position of the pigtail catheter can be used to penalize the detection score (output by the trained pigtail catheter detector) of each pigtail catheter candidate, and the pigtail catheter candidates can be re-ranked using the detection scores including the penalty function.

Figure 4A:
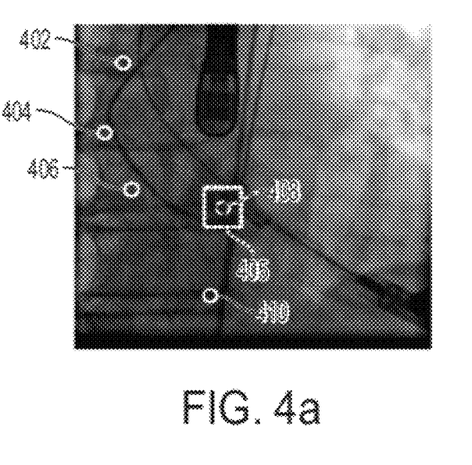
FIG. 4 illustrates exemplary pigtail catheter tip detection results using motion prediction.
Figure 4B:
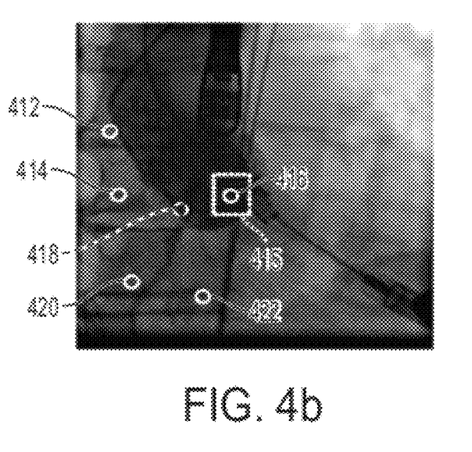

FIG. 4 illustrates exemplary pigtail catheter tip detection results using motion prediction. As shown in FIG. 4, images (a) and (b) illustrated pigtail catheter tip detection in two different frames of a fluoroscopic image sequence. As shown in image (a), pigtail catheter tip candidates 402, 404, 406, 408, and 410 are detected by a trained detector, with pigtail catheter tip candidate 408 being the candidate with the highest rank. Image (a) also shows a predicted searching range 405 determined based on a predicted pigtail catheter tip location for that frame using the ARMA model. In image (a), the highest ranked pigtail catheter candidate 408 is in the predicted searching rang 405. As shown in image (b), pigtail catheter tip candidates 412, 414, 416, 418, 420, and 422 are detected by a trained detector, with pigtail catheter tip candidate 418 being the candidate with the highest rank. Image (b) also shows a predicted searching range 415 determined based on a predicted pigtail catheter tip location for that frame using the ARMA model. In image (b), the highest ranked pigtail catheter tip candidate 418 is a false positive, and is not within the predicted searching range 415. Accordingly, constraining the pigtail catheter tip detection using the predicted search range 415 corrects the false detection and selects the correct pigtail catheter tip candidate 416 as the pigtail catheter tip location.

As described above, pigtail catheter motion prediction using the ARMA model is used to constrain the search in pigtail catheter tip tracking. This can be compared with a naïve way of propagating the last position of an object in a previous frame to the current frame as the predicted position. The naïve method assumes that the target has no motion from the previous frame to the current frame. If the true motion is small, the naïve method can give quite reasonable results. However, the cardiac motion and respiratory motion will always affect the pigtail catheter tip motion and the pigtail catheter tip motion can be quite large from frame to frame. Thus, the naïve method cannot follow the change in position and results in large errors, while the method described herein will follow the motion patterns and give better results. In some tracking methods, the naïve method may be used as a relaxed search range constraint. However, when motions are quite large, the relaxed area can increase dramatically to guarantee the true position is within this area, such that the naïve method does not provide significant advantages. The ARMA model used for motion prediction in embodiments of the present invention attempts to find the motion pattern and follow the pattern. Assuming that the model is fitted well to the previous observation, a search constraint with a smaller relaxing term can be used to reduce the search space for the pigtail catheter tip detector.

Figure 5A:
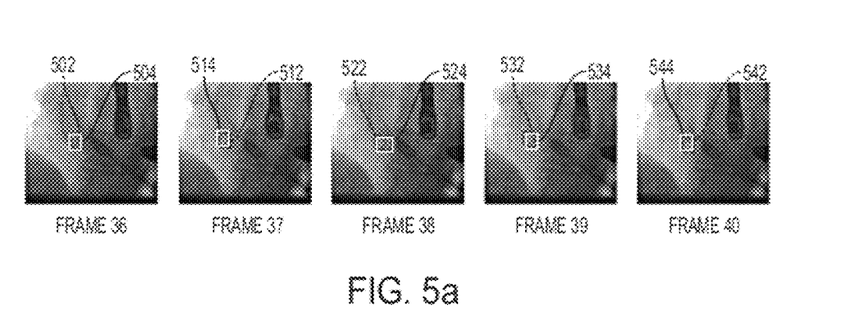
FIG. 5 illustrates exemplary pigtail catheter tip tracking results using different motion prediction techniques.
Figure 5B:
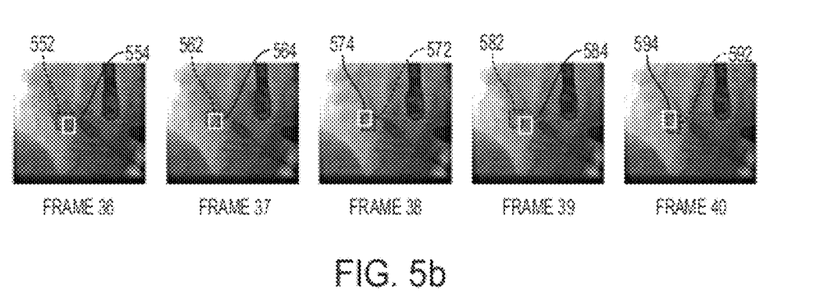

FIG. 5 illustrates exemplary pigtail catheter tip tracking results using different motion prediction techniques. As illustrated in FIG. 5, row (a) shows pigtail catheter tip tracking results in frames 36-40 of a fluoroscopic image sequence using the ARMA model to predict pigtail catheter motion, and row (b) shows pigtail catheter tip tracking results in frames 36-40 of the fluoroscopic image sequence using the naïve method which propagates the last frame position of the pigtail catheter tip to the current frame. In row (a), the ground truth pigtail catheter tip locations are shown in frames 36-40 as 502, 512, 522, 532, and 542, respectively, and the pigtail catheter tip detection results are shown in frames 36-40 as 504, 514, 524, 534, and 544, respectively. In row (b), the ground truth pigtail catheter tip locations are shown in frames 36-40 as 552, 562, 572, 582, and 592, respectively, and the pigtail catheter tip detection results are shown in frames 36-40 as 554, 564, 574, 584, and 594, respectively.

Figure 6A:
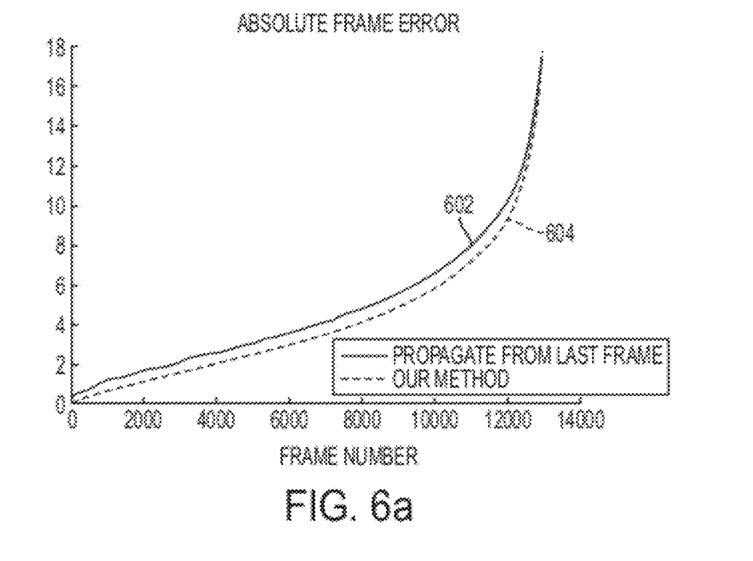
FIG. 6 illustrates frame errors for exemplary fluoroscopic image sequences.
Figure 6B:
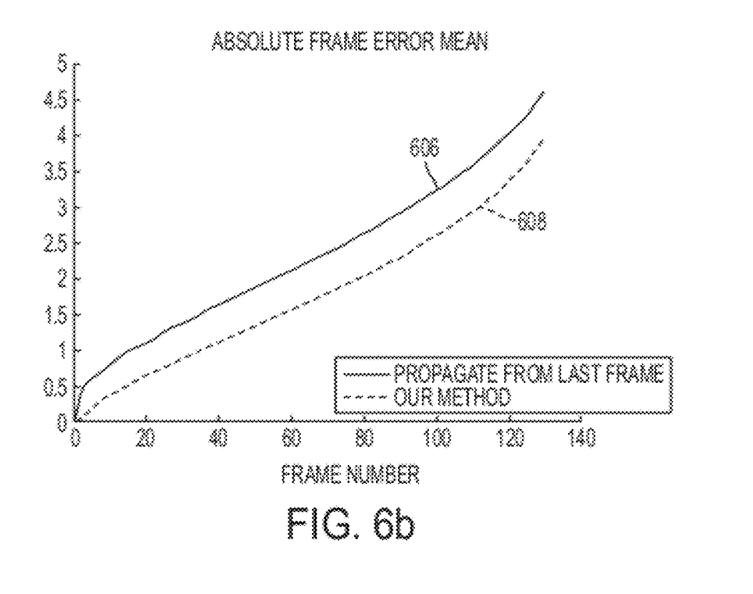

FIG. 6 illustrates frame errors for exemplary tested fluoroscopic image sequences using the ARMA model to estimate motion and the naïve method. Image (a) of FIG. 6 shows the absolute frame error using the naïve method 602 and the ARMA motion prediction method 604. Image (b) shows the absolute frame error mean using the naïve method 606 and the ARMA motion prediction method 608. The ARMA motion prediction method of FIG. 3 outperforms the naïve method. Under the 0.3 mm/pixel resolution, the mean error for the naïve method reaches 4.70 pixels, while the mean error of the ARMA motion modeling method reaches 4.04 pixels. As shown in image (a) of FIG. 6, there are less than 1% of the data in which the errors in the ARMA motion predicting method are higher than the in the naïve approach, which is caused by the linear prediction model assumption. During the prediction of the first few frames, the data is not sufficient enough for a full motion cycle. Therefore it cannot represent the real model accurately enough and results in a larger error at some point (e.g., the first peak or trough of a sine like motion).

Steps 306 and 308 of FIG. 3 may be repeated for each frame of a fluoroscopic image sequence to predict a pigtail catheter tip position in each frame and then detect the pigtail catheter tip position in each frame based on the prediction. In one embodiment, steps 306 and 308 are repeated for each frame and the method returns to step 304 after at a constant interval of frames to periodically refit the parameters of the ARMA model using all of the previous observations. In another embodiment, steps 304, 306, and 308 are repeated for each frame, such that the parameters of the ARMA model are refit for each frame before the ARMA model is used for predicting the pigtail catheter tip position in each frame in order to take into account the observation (pigtail catheter tip location) detected for the previous frame.

In addition to pigtail catheter tip tracking, the pigtail catheter tip motion prediction can be used for other applications as well. For example, the pigtail catheter tip motion prediction described above can be used for abnormal motion detection in a fluoroscopic image sequence. In many applications it is assumed that the pigtail catheter remains in a rigid connection with aorta or the aortic valve. However, during the aortic valve implantation surgery, physicians will need to adjust the pigtail catheter sometime to set it to a good pose. Also, at some point, the catheter needs to be pulled back from the aortic valve. In these cases, the rigid assumption will not hold anymore. Accordingly, it is beneficial to detect such a frame when the rigid assumption is violated.

Figure 7A:
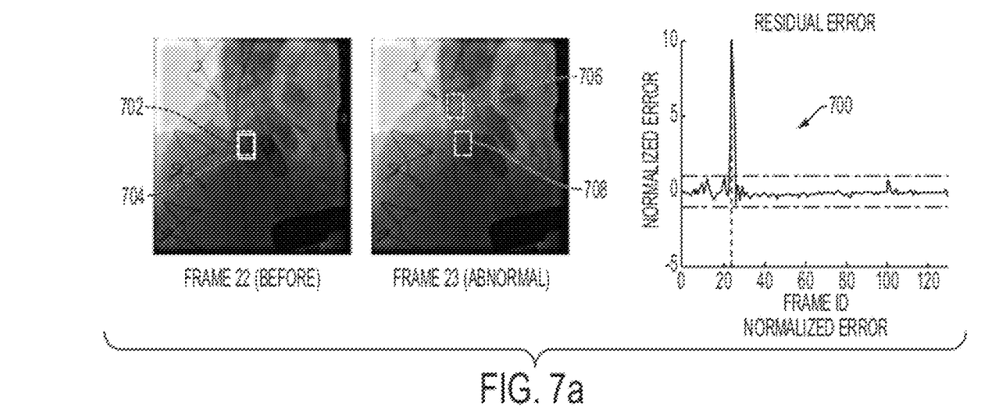
FIG. 7 illustrates abnormal motion detection in two exemplary fluoroscopic image sequences.
Figure 7B:
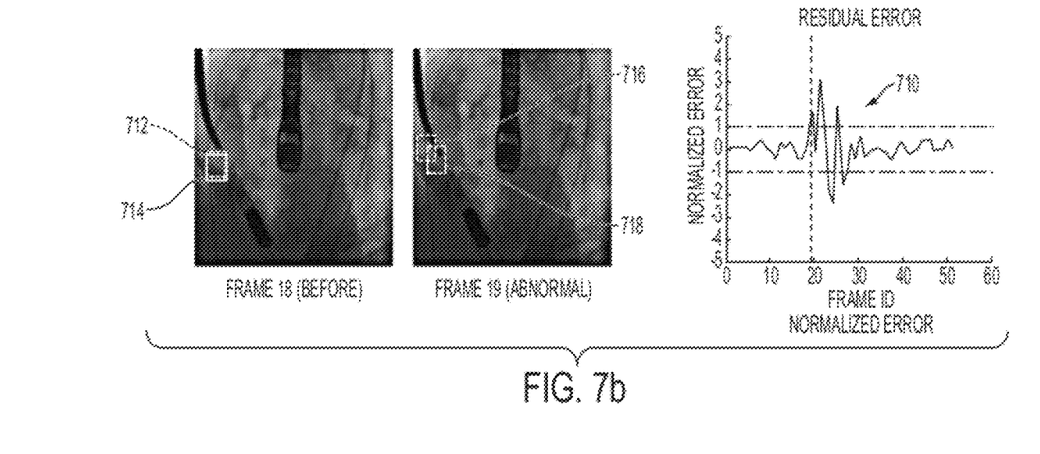

Using the autoregressive prediction model described above, the abnormal motion can be easily regarded as out-of-pattern motion. That is, after the model parameters are fit and a stable motion pattern acquired, if at any time the prediction result for the position of the pigtail catheter tip is far from the observation (e.g., above a certain threshold), then it can be determined that there occurs an abnormal motion. FIG. 7 illustrates abnormal motion detection in two exemplary fluoroscopic image sequences. Row (a) shows abnormal motion detection for a first sequence and row (b) shows abnormal motion detection for a second sequence. As shown in row (a), frame 22 of the fluoroscopic image sequence shows the ground truth pigtail catheter tip position detection result 702 and the predicted pigtail catheter tip position 704. At frame 23, abnormal motion is detected because the ground truth pigtail catheter tip position detection result 706 and the predicted pigtail catheter tip position 708 are further than a certain threshold apart. Image 700 is a residual error graph for frames of the fluoroscopic image sequence. As shown in row (b), frame 18 of the fluoroscopic image sequence shows the ground truth pigtail catheter tip position detection result 712 and the predicted pigtail catheter tip position 714. At frame 19, abnormal motion is detected because the ground truth pigtail catheter tip position detection result 716 and the predicted pigtail catheter tip position 718 are further than a certain threshold apart. Image 710 is a residual error graph for the frames of the fluoroscopic image sequence. As shown in FIG. 7, the residual error between prediction and observation is analyzed along the frame time. It is assumed the first few frames are without abnormal motion, so that the model can be built, and the maximum and minimum values to normalize the residual errors are determined. The abnormal motion will happen once we detect the error is above the threshold (e.g., 1 as in image 710).

Another application for the pigtail catheter motion prediction is for 2D/3D registration. 2D/3D registration is easy if both images are captured within a short period of time. However, in many situations, only the pre-operative CT (or C-arm CT) obtained one day or even earlier before the surgery is available. Accordingly, a sophisticated 2D/3D registration method is needed if the physicians want to use the early 3D CT data for guidance in the surgery. In most cases, the registration is performed on contrasted frames and is independent regardless of the temporal information. Since the registration is applied to each frame, it needs to make a global search first to decide the initial position for the next local search step. Introducing the motion prediction method described above as temporal information, the prediction result can be set as the initial position and used directly in the local search. This will save the computation in the global search and advance the speed of the registration. Furthermore, when there are non-contrasted frames (which are not registered) following the registered ones, the landmark can continue to be predicted until it appears in the contrasted frames that need to be registered. In this way, the previous information can be preserved and propagated to the current frame to save computation costs.

Figure 8:
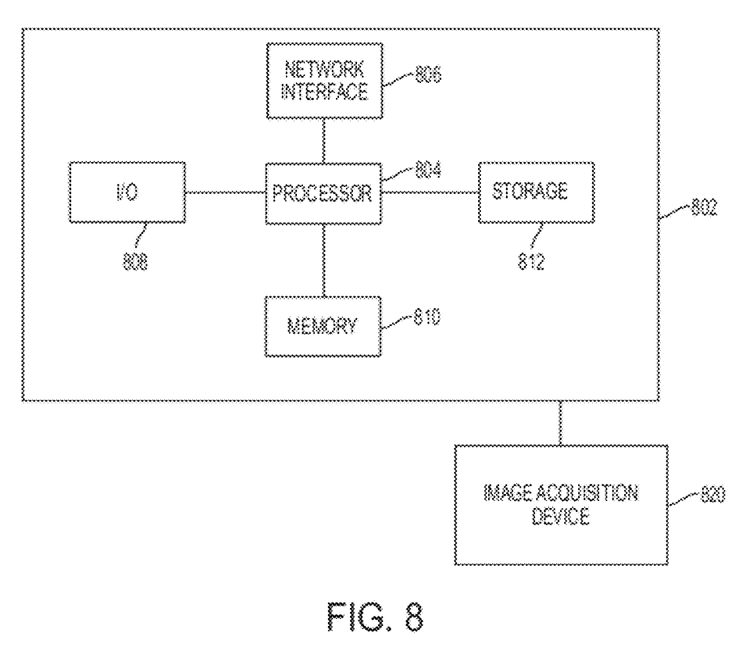
FIG. 8 is a high level block diagram of a computer capable of implementing the present invention.

The above-described methods for predicting motion of a pigtail catheter in a fluoroscopic image sequence may be implemented on a computer using well-known computer processors, memory units, storage devices, computer software, and other components. A high level block diagram of such a computer is illustrated in FIG. 8. Computer 802 contains a processor 804 which controls the overall operation of the computer 802 by executing computer program instructions which define such operation. The computer program instructions may be stored in a storage device 812, or other computer readable medium (e.g., magnetic disk, CD ROM, etc.) and loaded into memory 810 when execution of the computer program instructions is desired. Thus, the steps of the methods of FIG. 3, as well as the various applications for pigtail catheter motion prediction described above, may be defined by the computer program instructions stored in the memory 810 and/or storage 812 and controlled by the processor 804 executing the computer program instructions. An image acquisition device 820, x-ray scanning device, can be connected to the computer 802 to input images to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for predicting motion of a pigtail catheter in a fluoroscopic image sequence, comprising:
   fitting parameters of an autoregressive model based on observed pigtail catheter tip positions in a plurality of previous frames of the fluoroscopic image sequence;
   predicting a pigtail catheter tip position in a current frame of the fluoroscopic image sequence using the autoregressive model; and
   detecting the pigtail catheter tip position in the current frame based on the predicted pigtail catheter tip position using a trained learning-based pigtail catheter tip detector, wherein the detection of the pigtail catheter tip position in the current frame by the trained learning-based pigtail catheter tip detector is constrained by the predicted pigtail catheter tip position in the current frame and the step of detecting the pigtail catheter tip position in the current frame based on the predicted pigtail catheter tip position using a trained learning-based pigtail catheter tip detector comprises:
   detecting pigtail catheter tip position candidates in the current frame using the trained learning-based pigtail catheter tip detector, and
   penalizing a detection score calculated for each of the detected pigtail catheter tip position candidates by the trained pigtail catheter tip detector based on a penalty function centered at the predicted pigtail catheter tip position, wherein the penalty function is a 2D Gaussian distribution centered at the predicted pigtail catheter tip position.

2. The method of claim 1, wherein the autoregressive model is an autoregressive moving average (ARMA) model including an autoregressive part that predicts the pigtail catheter tip position in the current frame based on observed pigtail catheter tip positions in a first number of previous frames and a moving average part that adjusts the predicted pigtail catheter tip position in the current frame based on errors errors between predicted pigtail catheter tip positions and observed pigtail catheter tip positions in a second number of previous frames.

3. The method of claim 2, wherein the step of predicting a pigtail catheter location in a current frame of the fluoroscopic image sequence using the autoregressive model comprises:
   predicting the pigtail catheter location in the current frame as:

$$X_t = c + \varepsilon_t + \sum_{i=1}^{p} \alpha_i X_{t-i} + \sum_{i=1}^{q} \beta_i \varepsilon_{t-i}.$$

where $X_i$ denotes the pigtail catheter tip position in frame i, c is a constant, $\varepsilon_t$ denotes Gaussian white noise, $\alpha_i$ is a weighting coefficient for the observed pigtail catheter tip position of each previous frame, p is an order which indicates the first number of previous frames used in the autoregressive part, $\varepsilon_{t-i}$ is an error between an observed pigtail catheter tip position and a predicted pigtail catheter tip position for a previous frame t−i, $\beta_i$ is a weighting coefficient for the error of each previous frame, and q is an order which indicates the second number of previous frames used in the moving average part.

4. The method of claim 3, wherein the orders p and q are selected based on annotated training data.

5. The method of claim 3, wherein the step of fitting parameters of an autoregressive model based on observed pigtail catheter tip positions in a plurality of previous frames of the fluoroscopic image sequence comprises:
estimating c, $\alpha_i$, and $\beta_i$ based on the observed pigtail catheter tip positions in the plurality of previous frames of the fluoroscopic image sequence.

6. The method of claim 1, wherein the step of fitting parameters of an autoregressive model based on observed pigtail catheter tip positions in a plurality of previous frames of the fluoroscopic image sequence comprises:
estimating parameters of the autoregressive model to minimize a least square error between the observed pigtail catheter tip positions and predicted pigtail catheter tip positions using the autoregressive model in the plurality of previous frames of the fluoroscopic image sequence.

7. The method of claim 1, further comprising:
repeating the predicting and detecting steps for a plurality of next frames in the fluoroscopic image sequence.

8. The method of claim 7, further comprising:
repeating the fitting step after the pigtail catheter position is detected in a predetermined interval of frames.

9. The method of claim 1, further comprising:
repeating the fitting, predicting, and detecting steps for a plurality of next frames in the fluoroscopic image sequence.

10. The method of claim 1, further comprising:
detecting abnormal motion of the pigtail catheter in the current frame of the fluoroscopic image sequence based on the predicted pigtail catheter tip position.

11. The method of claim 10, wherein the step of detecting abnormal motion of the pigtail catheter in the current frame of the fluoroscopic image sequence based on the predicted pigtail catheter tip position comprises:
detecting an actual pigtail catheter tip location in the current frame;
calculating a residual error between the actual pigtail catheter tip location and the predicted pigtail catheter tip location in the current frame; and
detecting abnormal motion of the pigtail catheter in the current frame when the residual error is greater than a threshold.

12. The method of claim 1, wherein:
fitting parameters of an autoregressive model based on observed pigtail catheter tip positions in a plurality of previous frames of the fluoroscopic image sequence comprises:
fitting parameters of a first autoregressive model based on x-coordinates of the observed pigtail catheter tip positions in the plurality of previous frames, and
fitting parameters of a second autoregressive model based on y-coordinates of the observed pigtail catheter tip positions in the plurality of previous frames; and
predicting a pigtail catheter tip position in a current frame of the fluoroscopic image sequence using the autoregressive model comprises:
predicting an x-coordinate of the pigtail catheter tip position in the current frame using the first autoregressive model, and
predicting a y-coordinate of the pigtail catheter tip position in the current frame using the second autoregressive model.

13. An apparatus for predicting motion of a pigtail catheter in a fluoroscopic image sequence, comprising:
a processor; and
a memory storing computer program instructions, which when executed by the processor cause the processor to perform operations comprising:
fitting parameters of an autoregressive model based on observed pigtail catheter tip positions in a plurality of previous frames of the fluoroscopic image sequence;
predicting a pigtail catheter tip position in a current frame of the fluoroscopic image sequence using the autoregressive model; and
detecting the pigtail catheter tip position in the current frame based on the predicted pigtail catheter tip position using a trained learning-based pigtail catheter tip detector, wherein the detection of the pigtail catheter tip position in the current frame by the trained learning-based pigtail catheter tip detector is constrained by the predicted pigtail catheter tip position in the current frame and detecting the pigtail catheter tip position in the current frame based on the predicted pigtail catheter tip position using a trained learning-based pigtail catheter tip detector comprises:
detecting pigtail catheter tip position candidates in the current frame using the trained learning-based pigtail catheter tip detector, and
penalizing a detection score calculated for each of the detected pigtail catheter tip position candidates by the trained pigtail catheter tip detector based on a penalty function centered at the predicted pigtail catheter tip position, wherein the penalty function is a 2D Gaussian distribution centered at the predicted pigtail catheter tip position.

14. The apparatus of claim 13, wherein the autoregressive model is an autoregressive moving average (ARMA) model including an autoregressive part that predicts the pigtail catheter tip position in the current frame based on observed pigtail catheter tip positions in a first number of previous frames and a moving average part that adjusts the predicted pigtail catheter tip position in the current frame based on errors errors between predicted pigtail catheter tip positions and observed pigtail catheter tip positions in a second number of previous frames.

15. The apparatus of claim 14, wherein predicting a pigtail catheter location in a current frame of the fluoroscopic image sequence using the autoregressive model comprises:
predicting the pigtail catheter location in the current frame as:

$$X_t = c + \varepsilon_t + \sum_{i=1}^{p} \alpha_i X_{t-i} + \sum_{i=1}^{q} \beta_i \varepsilon_{t-i}.$$

where $X_i$ denotes the pigtail catheter tip position in frame i, c is a constant, $\varepsilon_t$ denotes Gaussian white noise, $\alpha_i$ is a weighting coefficient for the observed pigtail catheter tip position of each previous frame, p is an order which indicates the first number of previous frames used in the autoregressive part, $\varepsilon_{t-i}$ is an error between an observed pigtail catheter tip position and a predicted pigtail catheter tip position for a previous frame t−i, $\beta_i$ is a weighting coefficient for the error of each previous frame, and q is an order which indicates the second number of previous frames used in the moving average part.

16. The apparatus of claim 15, wherein fitting parameters of an autoregressive model based on observed pigtail catheter tip positions in a plurality of previous frames of the fluoroscopic image sequence comprises:
estimating c, $\alpha_i$, and $\beta_i$ based on the observed pigtail catheter tip positions in the plurality of previous frames of the fluoroscopic image sequence.

17. The apparatus of claim 13, wherein fitting parameters of an autoregressive model based on observed pigtail catheter tip positions in a plurality of previous frames of the fluoroscopic image sequence comprises:
estimating parameters of the autoregressive model to minimize a least square error between the observed pigtail catheter tip positions and predicted pigtail catheter tip positions using the autoregressive model in the plurality of previous frames of the fluoroscopic image sequence.

18. The apparatus of claim 13, wherein the operations further comprise:
detecting abnormal motion of the pigtail catheter in the current frame of the fluoroscopic image sequence based on the predicted pigtail catheter tip position.

19. The apparatus of claim 18, wherein detecting abnormal motion of the pigtail catheter in the current frame of the fluoroscopic image sequence based on the predicted pigtail catheter tip position comprises:
detecting an actual pigtail catheter tip location in the current frame;
calculating a residual error between the actual pigtail catheter tip location and the predicted pigtail catheter tip location in the current frame; and
detecting abnormal motion of the pigtail catheter in the current frame when the residual error is greater than a threshold.

20. A non-transitory computer readable medium encoded with computer executable instructions for predicting motion of a pigtail catheter in a fluoroscopic image sequence, the computer executable instructions defining steps comprising:
fitting parameters of an autoregressive model based on observed pigtail catheter tip positions in a plurality of previous frames of the fluoroscopic image sequence;
predicting a pigtail catheter tip position in a current frame of the fluoroscopic image sequence using the autoregressive model; and
detecting the pigtail catheter tip position in the current frame based on the predicted pigtail catheter tip position using a trained learning-based pigtail catheter tip detector, wherein the detection of the pigtail catheter tip position in the current frame by the trained learning-based pigtail catheter tip detector is constrained by the predicted pigtail catheter tip position in the current frame and detecting the pigtail catheter tip position in the current frame based on the predicted pigtail catheter tip position using a trained learning-based pigtail catheter tip detector comprises:
detecting pigtail catheter tip position candidates in the current frame using the trained learning-based pigtail catheter tip detector, and
penalizing a detection score calculated for each of the detected pigtail catheter tip position candidates the trained learning-based pigtail catheter tip detector based on a penalty function centered at the predicted pigtail catheter tip position, wherein the penalty function is a 2D Gaussian distribution centered at the predicted pigtail catheter tip position.

21. The non-transitory computer readable medium of claim 20, wherein the autoregressive model is an autoregressive moving average (ARMA) model including an autoregressive part that predicts the pigtail catheter tip position in the current frame based on observed pigtail catheter tip positions in a first number of previous frames and a moving average part that adjusts the predicted pigtail catheter tip position in the current frame based on errors errors between predicted pigtail catheter tip positions and observed pigtail catheter tip positions in a second number of previous frames.

22. The non-transitory computer readable medium of claim 21, wherein the computer executable instructions defining the step of predicting a pigtail catheter location in a current frame of the fluoroscopic image sequence using the autoregressive model comprise computer executable instructions defining the step of:
predicting the pigtail catheter location in the current frame as:

$$X_t = c + \varepsilon_t + \sum_{i=1}^{p} \alpha_i X_{t-i} + \sum_{i=1}^{q} \beta_i \varepsilon_{t-i}.$$

where $X_i$ denotes the pigtail catheter tip position in frame i, c is a constant, $\varepsilon_t$ denotes Gaussian white noise, $\alpha_i$ is a weighting coefficient for the observed pigtail catheter tip position of each previous frame, p is an order which indicates the first number of previous frames used in the autoregressive part, $\varepsilon_{t-i}$ is an error between an observed pigtail catheter tip position and a predicted pigtail catheter tip position for a previous frame t–i, $\beta_i$ is a weighting coefficient for the error of each previous frame, and q is an order which indicates the second number of previous frames used in the moving average part.

23. The non-transitory computer readable medium of claim 22, wherein the computer executable instructions defining the step of fitting parameters of an autoregressive model based on observed pigtail catheter tip positions in a plurality of previous frames of the fluoroscopic image sequence comprise computer executable instructions defining the step of:
estimating c, $\alpha_i$, and $\beta_i$ based on the observed pigtail catheter tip positions in the plurality of previous frames of the fluoroscopic image sequence.

24. The non-transitory computer readable medium of claim 20, wherein the computer executable instructions defining the step of fitting parameters of an autoregressive model based on observed pigtail catheter tip positions in a plurality of previous frames of the fluoroscopic image sequence comprise computer executable instructions defining the step of:
estimating parameters of the autoregressive model to minimize a least square error between the observed pigtail catheter tip positions and predicted pigtail catheter tip positions using the autoregressive model in the plurality of previous frames of the fluoroscopic image sequence.

25. The non-transitory computer readable medium of claim 20, further comprising computer executable instructions defining the step of:
detecting abnormal motion of the pigtail catheter in the current frame of the fluoroscopic image sequence based on the predicted pigtail catheter tip position.

26. The non-transitory computer readable medium of claim 25, wherein the computer executable instructions defining the step of detecting abnormal motion of the pigtail catheter in the current frame of the fluoroscopic image sequence based on the predicted pigtail catheter tip position comprise computer executable instructions defining the steps of:
  detecting an actual pigtail catheter tip location in the current frame;
  calculating a residual error between the actual pigtail catheter tip location and the predicted pigtail catheter tip location in the current frame; and
  detecting abnormal motion of the pigtail catheter in the current frame when the residual error is greater than a threshold.

* * * * *